US00PP31242P2

(12) United States Plant Patent
Yu et al.

(10) Patent No.: US PP31,242 P2
(45) Date of Patent: Dec. 17, 2019

(54) ***NELUMBO* PLANT NAMED 'YANZHUANG ZHAOJUN'**

(50) Latin Name: *Nelumbo nucifera*
Varietal Denomination: Yanzhuang Zhaojun

(71) Applicants: Dongbei Yu, Hangzhou (CN); Yanrong Fu, Hangzhou (CN)

(72) Inventors: Dongbei Yu, Hangzhou (CN); Yanrong Fu, Hangzhou (CN)

(73) Assignee: Zhejiang Renwen Landscape Architecture Co., Ltd., Hangzhou (CN)

( * ) Notice: Subject to any disclaimer, the term of this patent is extended or adjusted under 35 U.S.C. 154(b) by 0 days.

(21) Appl. No.: 16/350,036

(22) Filed: Sep. 18, 2018

(51) Int. Cl.
*A01H 5/02* (2018.01)

(52) U.S. Cl.
USPC ..... Plt./342

(58) Field of Classification Search
USPC ..... Plt./342
CPC ..... A01H 6/00; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Nelumbo* plant named 'Yanzhuang Zhaojun', characterized by its upright plant habit; moderately vigorous growth habit; large medium green-colored leaves; freely flowering habit; and large red purple and white bi-colored globose-shaped flowers that are positioned above the foliar plane on moderately strong and erect peduncles.

2 Drawing Sheets

Botanical designation: *Nelumbo nucifera.*
Cultivar denomination: 'YANZHUANG ZHAOJUN'.

CROSS-REFERENCED TO CLOSELY-RELATED APPLICATIONS

Title: *Nelumbo* Plant Named 'Zhijiang Qiuyue'
Applicants: Xun Zhao & Yuchu Chen
Filed: Concurrently with this application

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Yanzhuang Zhaojun'.

The new *Nelumbo* plant is a product of a controlled breeding program conducted by the Inventors in Hangzhou, Zhejiang, China. The objective of the breeding program is to create new *Nelumbo* plants that have attractive and unique flower forms and flower colors.

The new *Nelumbo* plant originated from a cross-pollination in July, 2013 of *Nelumbo nucifera* 'Youyi Mudan', not patented, as the female, or seed, parent with *Nelumbo nucifera* 'Ziqi Xilai', not patented, as the male, or pollen, parent. The new *Nelumbo* plant was discovered and selected by the Inventors as a single flowering plant within the progeny of the stated open-pollination in a controlled greenhouse environment in Hangzhou, Zhejiang, China in July, 2015.

Asexual reproduction of the new *Nelumbo* plant by rhizome divisions in a controlled environment in Hangzhou, Zhejiang, China since April, 2017 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Yanzhuang Zhaojun'. These characteristics in combination distinguish 'Yanzhuang Zhaojun' as a new and distinct *Nelumbo* plant:

1. Upright plant habit.
2. Moderately vigorous growth habit.
3. Large medium green-colored leaves.
4. Freely flowering habit.
5. Large red purple and white bi-colored globose-shaped flowers that are positioned above the foliar plane on moderately strong and erect peduncles.

Plants of the new *Nelumbo* differ from plants of the female parent, 'Youyi Mudan', in the following characteristics:

1. Plants of the new *Nelumbo* are smaller than plants of 'Youyi Mudan'.
2. Flowers of plants of the new *Nelumbo* have red purple and white bi-colored petals and petaloids whereas flowers of plants of 'Youyi Mudan' have light orange-colored petals and petaloids.

Plants of the new *Nelumbo* differ primarily from plants of the male parent, 'Ziqi Xilai' in flower color as flowers of plants of the new *Nelumbo* have bi-colored petals and petaloids whereas petals and petaloids of flowers of plants of 'Ziqi Xilai' are not bi-colored.

Plants of the new *Nelumbo* differ primarily from plants of *Nelumbo nucifera* 'Zhijiang Qiuyue', disclosed in a U.S. Plant Patent application filed concurrently, in flower color as flowers of plants of the new *Nelumbo* have red purple and white bi-colored petals and petaloids whereas petals and petaloids of flowers of plants of 'Zhijiang Qiuyue' are pale yellow and green white in color.

Plants of the new *Nelumbo* can be compared to plants of *Nelumbo nucifera* 'Zhaojun Guying', not patented. In side-by-side comparisons plants of the new *Nelumbo* differ primarily from plants of 'Zhaojun Guying' in the following characteristics:

1. Flowers of plants of the new *Nelumbo* have twice as many petals and petaloids as flowers of plants of 'Zhaojun Guying'.
2. Flowers of plants of the new *Nelumbo* have red purple and white bi-colored petals and petaloids whereas flowers of plants of 'Zhaojun Guying' have light violet-colored petals and petaloids.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant. The photograph on the first sheet is a side perspective view of a typical plant of 'Yanzhuang Zhaojun' grown in a container. The photograph on the second sheet is a close-up view of a typical flower of 'Yanzhuang Xhaojun'.

DETAILED BOTANICAL DESCRIPTION

The aforementioned photographs and following observations and measurements describe plants grown during the summer in 37-cm by 35-cm containers in an outdoor nursery in Hangzhou, Zhejiang, China and under cultural practices typical of commercial *Nelumbo* production. During the production of the plants, day temperatures ranged from 14° C. to 33° C. and night temperatures ranged from 16° C. to 28° C. Plants were one year old when the photographs and the detailed description were taken. In the following description, color references are made to The Royal Horticultural Society Colour Chart, 2007 Edition, except where general terms of ordinary dictionary significance are used.

Botanical Classification: *Nelumbo nucifera* 'Yanzhuang Zhaojun'.

Parentage:

*Female, or seed, parent.*—*Nelumbo nucifera* 'Youyi Mudan', not patented.

*Male, or pollen, parent.*—*Nelumbo nucifera* 'Ziqi Xilai', not patented.

Propagation:

*Type.*—By rhizome divisions.

*Time to initiate roots, summer.*—About five days at temperatures about 27° C.

*Time to produce a rooted young plant.*—About eight days at temperatures about 27° C.

*Root description.*—Fine, fleshy; typically white to grey brown in color, actual color of the roots is dependent on water quality, fertilizer type and formulation, substrate temperature and physiological age of roots.

*Rooting habit.*—Not freely branching, medium density.

Plant Description:

*Plant and growth habit.*—Upright plant habit; moderately vigorous growth habit and moderate growth rate.

*Plant height* (*soil level to top of foliar plane*).—About 91 cm.

*Plant height* (*soil level to top of floral plane*).—About 102 cm.

*Plant diameter.*—About 140 cm by 110 cm.

Rhizome Description:

*Arrangement and habit.*—Sympodial branching habit with about ten primary branches developing per plant each with about three to ten secondary branches.

*Length.*—About 70 cm to 160 cm.

*Diameter.*—About 1.2 cm to 5.1 cm.

*Internode length.*—About 9 cm to 31 cm.

*Texture and luster.*—Smooth, glabrous; glossy.

*Color.*—White, close to 155B.

Leaf Description:

*Length, fully expanded.*—About 27 cm to 39 cm.

*Width, fully expanded.*—About 23 cm to 33 cm.

*Shape.*—Peltate, orbicular.

*Apex.*—Retuse.

*Base.*—Cuneate.

*Margin.*—Entire; undulate.

*Venation.*—Palmate.

*Texture and luster, upper and lower surfaces.*—Pubescent, papery; moderately glossy.

*Color.*—Developing leaves, upper surface: Close to 143A. Developing leaves, lower surface: Close to 138D. Fully expanded leaves, upper surface: Close to N137D; venation, close to 137A. Fully expanded leaves, lower surface: Close to N138B; venation, close to 144A.

*Petioles.*—Length: About 74 cm. Diameter: About 4 mm to 6 mm. Strength: Moderately strong. Texture and luster, upper and lower surfaces: Smooth, glabrous; moderately glossy. Color: Close to 144B.

Inflorescence Description:

*Arrangement.*—Double-type globose-shaped flowers developing directly from the rhizomes with numerous showy petals and petaloids; about 16 flower buds and flowers developing per plant at one time.

*Time to flower.*—In China, plants flower from June to August; flowering continuous during this period; flowers begin opening at 05:00 hours in the morning, flowers are fully opened at about 06:30 hours and are typically closed by 09:00 hours.

*Flower longevity.*—Flowers last about four days on the plant; flowers last about three days as a cut flower; flowers persistent; plants maintain good substance for about 50 days.

*Fragrance.*—Initially, very faint and then not detectable.

*Flower buds.*—Length: About 8 cm. Diameter: About 5 cm. Shape: Ovate. Texture and luster: Smooth, glabrous; matte. Color: Close to 73C.

*Flowers.*—Shape and arrangement: Double-type, globose-shaped with numerous showy petals and petaloids. Diameter: About 12 cm. Height: About 9.3 cm.

*Petals.*—Quantity and arrangement: About 260 arranged in numerous whorls. Length: About 10.3 cm. Width: About 4.9 cm. Shape: Obovate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening, upper and lower surfaces: Distally, close to 64A; mid-section and towards the base, close to NN155D; at the base, close to 8D. Fully opened, upper surface: Distally, close to 64A; mid-section and towards the base, close to NN155D;

at the base, close to 8D; venation, similar to lamina colors, close to 64A, NN155D and 8D; color becoming closer to 156C with development. Fully opened, lower surface: Close to 64C; venation, close to 64C; color becoming closer to 156C with development.

*Petaloids.*—Quantity and arrangement: About 245 arranged in numerous whorls. Length: About 5.3 cm. Width: About 4 mm. Shape: Oblanceolate. Apex: Obtuse. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening, upper and lower surfaces: Distally, close to 64A; mid-section and towards the base, close to NN155D; at the base, close to 8D. Fully opened, upper surface: Distally, close to 64A; mid-section and towards the base, close to NN155D; at the base, close to 8D; venation, similar to lamina colors, close to 64A, NN155D and 8D; color becoming closer to 156C with development. Fully opened, lower surface: Close to 64C; venation, close to 64C; color becoming closer to 156C with development.

*Sepals.*—Quantity and arrangement: About six in a single whorl. Length: About 6.7 cm. Width: About 3.8 cm. Shape: Obovate. Apex: Acuminate. Base: Cuneate. Texture and luster, upper and lower surfaces: Smooth, glabrous; matte. Color: When opening, upper and lower surfaces: Distally, close to 64A; mid-section and towards the base, close to NN155D; at the base, close to 8D. Fully opened, upper and lower surfaces: Distally, close to 64A; mid-section and towards the base, close to NN155D; at the base, close to 8D.

*Peduncles.*—Length: About 108 cm. Diameter: About 1.2 cm to 1.9 cm. Strength: Moderately strong. Aspect: Mostly erect. Texture and luster: Smooth, glabrous; slightly glossy. Color: Close to 138C.

*Stamens.*—Quantity per flower: About 34 to 73. Filament length: About 3.4 cm. Filament color: Close to 4C. Anther length: About 2.1 cm. Anther width: About 3 mm. Anther shape: Lanceolate. Anther color: Close to 6C. Pollen amount: Moderate. Pollen color: Close to 6C.

*Pistils.*—Quantity per flower: About 13. Pistil length: About 6.8 cm. Style length: About 2.9 cm. Style color: Close to 1A. Stigma diameter: About 1 mm. Stigma shape: Rounded. Stigma color: Close to 6B. Ovary color: Close to 145A.

*Fruits.*—Quantity per plant: About 32. Length: About 4.7 cm. Diameter: About 8.8 cm. Texture: Smooth, glabrous. Color: Close to 138B.

*Seeds.*—To date, seed development has not been observed on plants of the new *Nelumbo*.

Pathogen & Pest Resistance: To date, plants of the new *Nelumbo* have not been observed to be resistant to pathogens or pests common to *Nelumbo* plants.

Temperature Tolerance: Plants of the new *Nelumbo* have been observed to be tolerant to temperatures ranging from about −5° C. to about 41° C.

It is claimed:

1. A new and distinct *Nelumbo* plant named 'Yanzhuang Zhaojun' as illustrated and described.

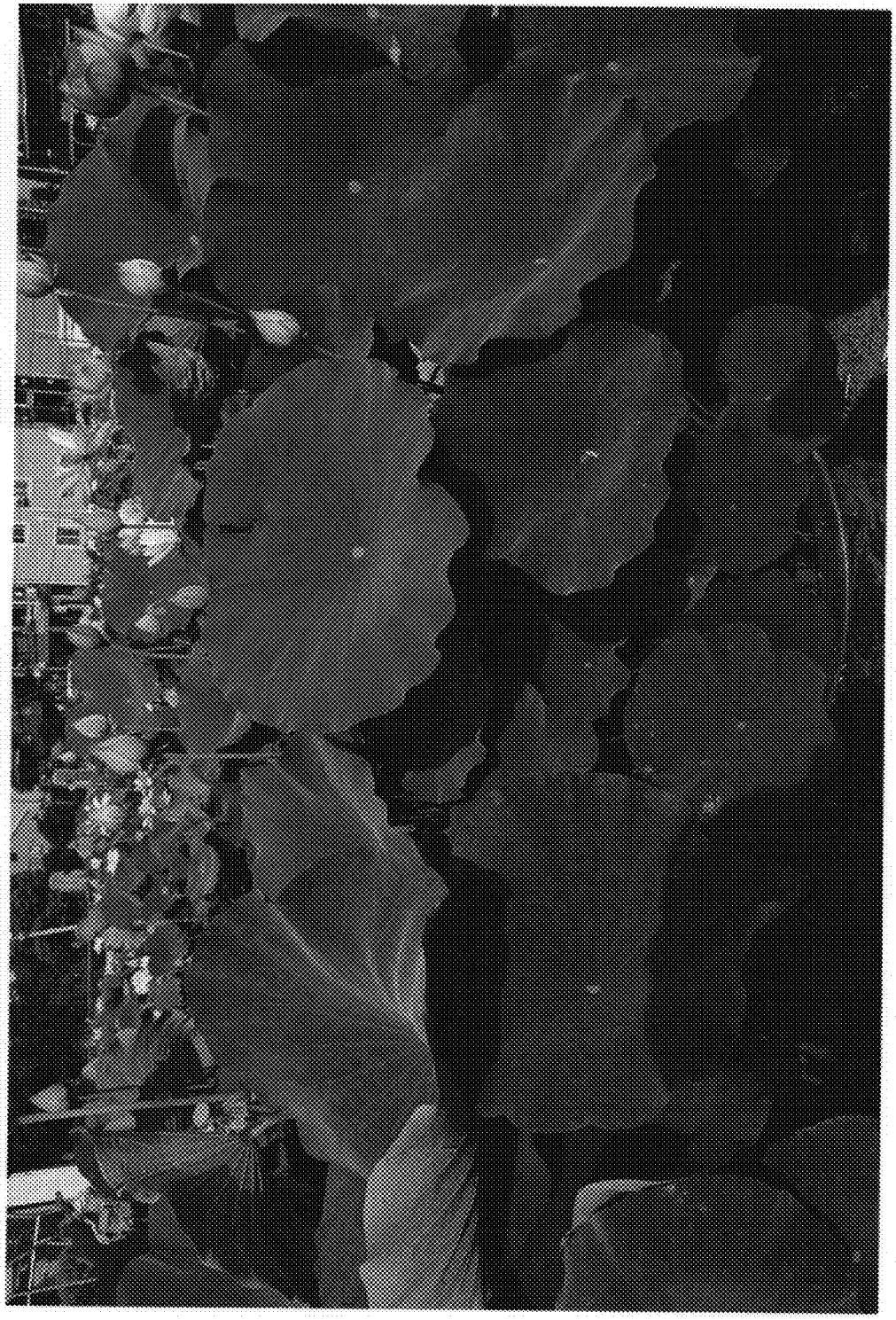

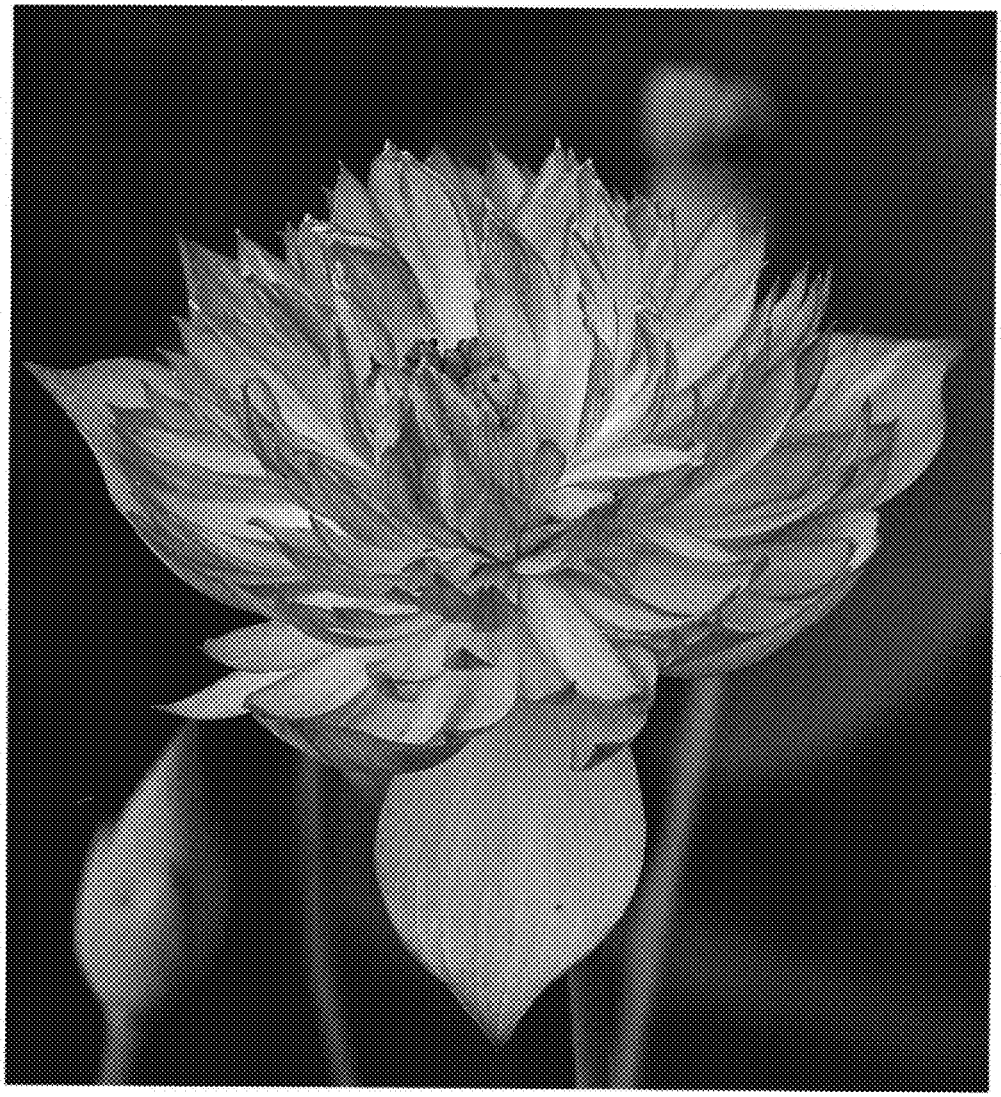

* * * * *